United States Patent [19]

Goldenberg

[11] Patent Number: 4,641,912

[45] Date of Patent: Feb. 10, 1987

[54] EXCIMER LASER DELIVERY SYSTEM, ANGIOSCOPE AND ANGIOPLASTY SYSTEM INCORPORATING THE DELIVERY SYSTEM AND ANGIOSCOPE

[76] Inventor: Tsvi Goldenberg, 2436 Washington St., Allentown, Pa. 18104

[21] Appl. No.: 679,538

[22] Filed: Dec. 7, 1984

[51] Int. Cl.$^4$ .................. A61N 5/06; G02B 23/26
[52] U.S. Cl. .................... 350/96.10; 128/6; 350/96.15; 350/96.26; 604/21; 604/53
[58] Field of Search ............ 350/96.10, 96.15, 96.24, 350/96.25, 96.26, 96.34; 128/6, 303.1; 604/20, 21, 53; 219/121 L, 121 LM, 121 LZ

[56] References Cited

U.S. PATENT DOCUMENTS

| | | | |
|---|---|---|---|
| 4,011,403 | 3/1977 | Epstein et al. | 350/96.10 X |
| 4,173,393 | 11/1979 | Maurer | 350/96.34 |
| 4,207,874 | 6/1980 | Choy | 128/6 |
| 4,248,213 | 2/1981 | Landre | 128/6 |
| 4,266,548 | 5/1981 | Davi | 128/303.1 |
| 4,305,640 | 12/1981 | Cullis et al. | 350/96.10 |
| 4,398,790 | 8/1983 | Righini et al. | 350/96.10 X |
| 4,418,688 | 12/1983 | Loeb | 128/6 |
| 4,521,070 | 6/1985 | Sottini et al. | 350/96.15 |

FOREIGN PATENT DOCUMENTS 2517019 10/1976 Fed. Rep. of Germany ... 350/96.18
2095422 9/1982 United Kingdom ............ 350/96.10

OTHER PUBLICATIONS

Linsker et al, "Far-Ultraviolet Laser Ablation of Atherosclerotic Lesions", *Lasers in Surgery and Medicine*, 4:201–206, Jul. 25, 1984.

Primary Examiner—John Lee
Attorney, Agent, or Firm—Burns, Doane, Swecker & Mathis

[57] ABSTRACT

A system for the delivery of high power excimer laser energy includes an optical fiber of pure silica having an energy coupler at one end and a lens at the distal end. The energy coupler can be a funnel-shaped input to the fiber or it can be a water-filled cavity which acts as a buffer to decrease the apparent density of energy entering the fiber. The lens at the distal end of the fiber functions to concentrate the output beam so as to increase its density. The delivery system has particular utility in the field of angioplasty. In such an application, the delivery system can be used to transmit both laser and illuminating light so as to reduce the number of optical fibers that are required and thereby provide a system that is sufficiently small to be fed into a coronary artery. An ultra-thin image scope facilitates a determination of the distance of the distal end from the viewed object and hence the size of the object.

16 Claims, 8 Drawing Figures

EXCIMER LASER DELIVERY SYSTEM, ANGIOSCOPE AND ANGIOPLASTY SYSTEM INCORPORATING THE DELIVERY SYSTEM AND ANGIOSCOPE

BACKGROUND OF THE INVENTION

The present invention is directed to a system for delivering high energy laser by means by an optical waveguide, and in one particular application is concerned with laser angioplasty.

The use of laser energy to ablate atherosclerotic plaque that forms an obstruction in a blood vessel is presently being investigated as a viable alternative to coronary bypass surgery. This procedure, known as angioplasty, essentially involves insertion of a fiberoptic waveguide into the vessel, and conduction of laser energy through the waveguide to direct it at the plaque once the distal end of the waveguide is positioned adjacent the obstruction. In order to enable the physician to ascertain the location of the waveguide as it is being moved through the vessel, additional waveguides for providing a source of illuminating light and for conducting the image from inside the vessel back to the physician are fed together with the laser waveguide. Typically, the three waveguides are encapsulated within a catheter.

Most of the experimentation and testing that has been done in this area has utilized continuous wave laser energy, such as that produced by Argon Ion, Nd:YAG or Carbon Dioxide lasers. The light produced by this type of laser is at a relatively low energy level. Ablation of the obstruction is achieved with these types of lasers by heating the plaque with the laser energy over a period of time until the temperature is great enough to destroy it.

While the use of continuous wave laser energy has been found to be sufficient to ablate an obstruction, it is not without its drawbacks. Most significantly, the removal of the obstruction is accompanied by thermal injury to the vessel walls immediately adjacent the obstruction. In an effort to avoid such thermal injury, the use of a different, higher level form of laser energy having a wavelength in the ultra-violet range (40–400 nanometers) has been suggested. This energy, known as Excimer laser energy, can be provided, for example, by a laser medium such as argon-chloride having a wavelength of 193 nanometers, krypton-chloride (222 nm), krypton-fluoride (240 nm) or xenon-chloride (308 nm). The output energy from this type of laser appears in short bursts or pulses that can last for 10–85 nanoseconds and have a high peak energy, for example as much as 200 mJ. Although the destruction mechanism involving this form of energy is not completely understood, it has been observed that one pulse of the Excimer laser produces an incision which destroys the target tissue without accompanying thermal injury to the surrounding area. This result has been theorized to be due to either or both of two phenomena. The delivery of the short duration, high energy pulses may vaporize the material so rapidly that heat transfer to the non-irradiated adjacent tissue is minimal. Alternatively, or in addition, ultraviolet photons absorbed in the organic material might disrupt molecular bonds to remove tissue by photochemical rather than thermal mechanisms.

While the high peak energy provided by the Excimer laser has been shown to provide improved results with regard to the ablation of atherosclerotic plaque, this characteristic of the energy also presents a serious practical problem. Specifically, a laser pulse having sufficient energy density to destroy an obstructing tissue also tends to destroy an optical fiber. The high energy density pulses break the fiber tip at the input end, first at the glass/air interface. Continued application of the laser energy causes a deep crater to be formed inside the fiber. Thus, it is not possible to deliver high-power ultraviolet laser energy in vivo using a conventional system designed for continuous wave laser energy.

This problem associated with the delivery of high energy Excimer laser pulses is particularly exacerbated in the field of angioplasty because of the small optical fibers that must be used. A coronary artery typically has an internal diameter of two millimeters or less. Accordingly, the total external diameter of the angioplasty system must be below two millimeters. If this system is composed of three separate optical fibers arranged adjacent one another, it will be appreciated that each individual fiber must be quite small in cross-sectional area.

A critical parameter with regard to the destruction of an optical fiber is the density of the energy that is presented to the end of the fiber. In order to successfully deliver the laser energy, the energy density must be maintained below the destruction threshold of the fiber, which might be around 25–30 $mJ/mm^2$. Thus, it will be appreciated that fibers having a small cross-sectional area, such as those used in angioplasty, can conduct only a limited amount of energy if the density level is maintained below the threshold value. This limited amount of energy may not be sufficient to ablate the obstructing tissue or plaque.

OBJECTS AND BRIEF STATEMENT OF THE INVENTION

Accordingly, it is a general object of the invention to provide a novel system for delivering high energy Excimer laser energy using an optical waveguide.

It is a more specific object of the invention to provide such a delivery system that is particularly well suited to deliver Excimer laser energy in vivo for the ablation of atherosclerotic plaque.

It is a further object of the invention to provide a novel angioplasty system.

It is another object of the invention to provide a novel image scope that can be used in an angioplasty system.

Briefly, in accordance with one aspect of the present invention, the delivery of high energy Excimer laser light by means of an optical waveguide is carried out by using a three-step approach. The first step is the selection of a proper material for the waveguide itself. It has been found that an optical fiber having a core of pure silica works best for the transmission of high energy ultraviolet laser light. Preferably, the fiber is a multimode fiber having a high core to cladding area ratio.

As a second step, the density of the energy that is conducted within the waveguide is increased by means of an energy coupler at the input end of the optical fiber. In one embodiment of the invention, this energy coupler comprises a container of liquid that essentially functions as a buffer to protect the input end of the fiber and enable energy of a higher density to be presented thereto. In a second embodiment of the invention, the energy coupler is provided by designing the input end of the fiber in a funnel shape so that the end of the fiber has a relatively large cross-sectional area which tapers down to the small diameter fiber needed for the desired application.

The third step that is utilized in the context of the present invention is to increase the density of the energy once it exits the fiber at the distal end. This increase is provided by means of a lens on the fiber itself. This lens can be produced by melting the flat polished tip of the fiber to a predetermined spherical curvature. The lens causes the laser beam to converge on a focal spot that is smaller than the fiber itself, thus reducing the beam area and increasing its energy density.

In accordance with another aspect of the present invention, the characteristic pattern of the light which exits from the lensed distal end of the optical fiber is utilized to provide a novel angioplasty system. Basically, the system utilizes only two optical fibers to perform the three functions of illumination, lasing and imaging. One optical fiber is dedicated to the imaging function. The other optical fiber conducts both visible light energy and the laser energy to accommodate the two functions of illumination and lasing. The use of only two fibers enables a fiber of larger diameter to be utilized than those which can be accommodated in a three-fiber angioplasty system.

In a third aspect of the invention, the angle of the illuminating light is adjusted relative to the field of view of the image waveguide to provide a reference viewing plane which enables a physician to determine the location of the distal end of the waveguide relative to an object being viewed, and hence the size of the object. Preferably, the beam of illuminating light intersects the field of view at a reference plane to allow the physician to determine when the viewed object is located at a preset distance from the end of the image guide.

Further features and advantages of the present invention will become apparent from the following detailed description of preferred embodiments of the invention illustrated in the accompanying drawings.

DESCRIPTION OF THE ILLUSTRATED EMBODIMENTS

In the following description of preferred embodiments of the invention, an Excimer laser delivery system is described with particular reference to its use in an angioplasty system, in order to facilitate an understanding of the invention and its uses. However, it will be appreciated that the practical applications of the delivery system are not limited to this single environment. Rather, the invention, in its broader aspects, can find utility in any application in which it is desirable to deliver high peak energy ultraviolet laser light by means of a fiber-optic waveguide, such as in a cutting tool or in arthroscopy for example.

Figure 1:
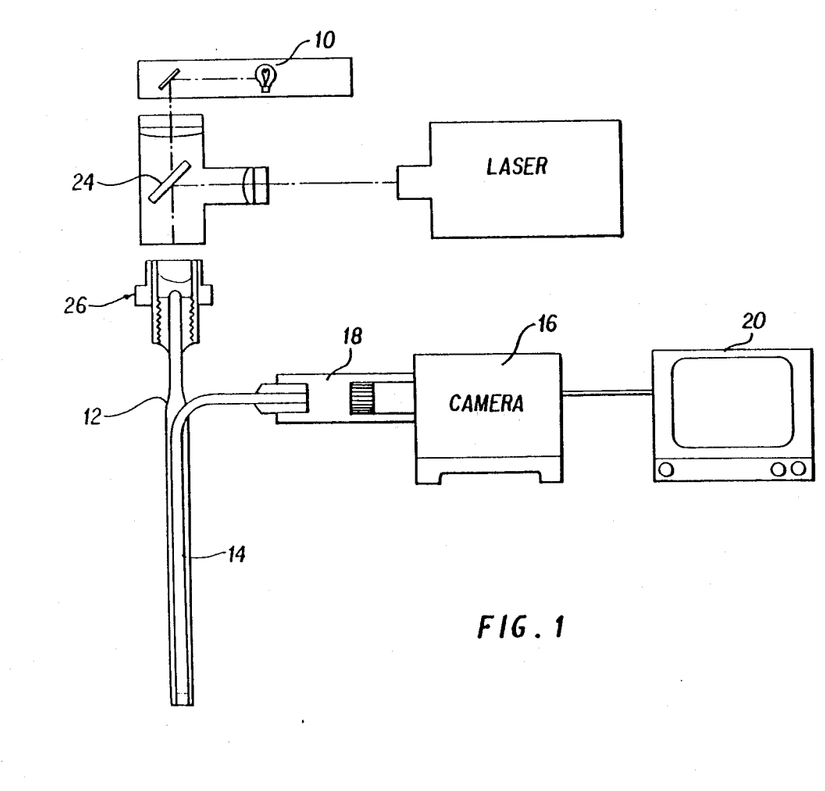
FIG. 1 is a schematic diagram of a laser and image delivery system that can be used for angioplasty.

Referring to FIG. 1, an angioplasty arrangement that can employ the delivery system of the present invention is shown in schematic form. The angioplasty system must be capable of performing three functions within the blood vessel. The first two of these relate to the illumination and imaging of the interior of the vessel to enable a physician to successfully propagate the distal end of the system through the vessel to the location of the obstruction. Accordingly, the output from a source of visible light, such as a Halogen or Xenon lamp 10, is directed to the input end of an optical fiber 12. The other (distal) end of this fiber is housed within a catheter (not shown) to enable it to be fed through a blood vessel. A second optical fiber 14 located adjacent the fiber 12 within the catheter receives the image from the illuminated interior of the blood vessel and transmits it to a video camera 16 by means of a video coupler 18 connected between the output end of the fiber 14 and the camera. The image presented to the camera 16 by the fiber 14 is converted into a video signal and fed to a suitable monitor 20 for viewing by the physician as the catheter is being positioned inside the blood vessel. Alternatively, the video coupler, camera and monitor can be replaced by an eyepiece that is attached to the output end of the fiber 14.

Once the distal ends of the fibers 12 and 14 have been appropriately positioned adjacent the obstruction, a high energy laser, such as an Excimer or Argon laser, is activated to ablate the obstruction. In a preferred form of the invention, the laser energy is conducted along the same optical fiber 12 as the visible light. To accomplish such a result, the output of the laser is directed at a beam splitter 24 which also transmits the visible light from the source 10. These two forms of light energy are propagated along the same path and presented to the input end of the optical fiber 12 by means of an energy coupler 26.

Figure 2:
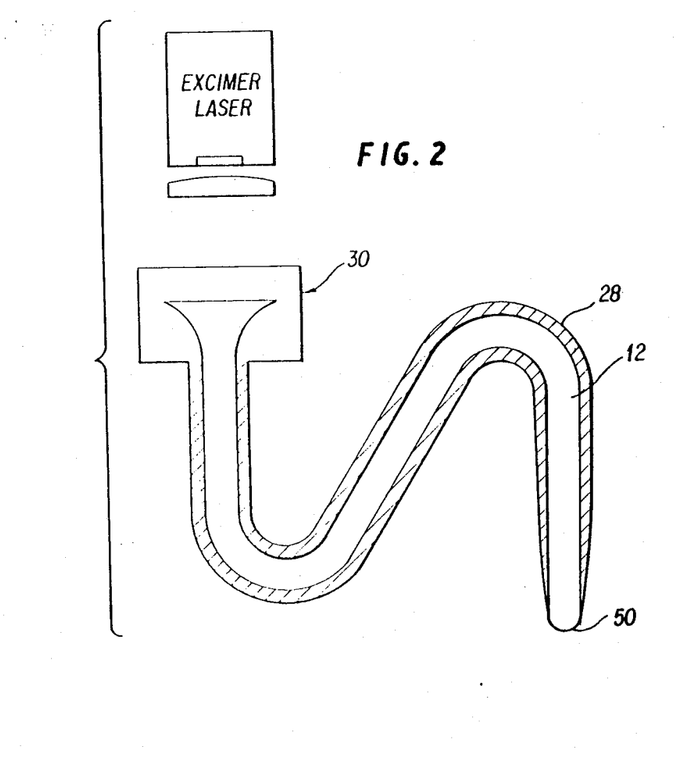
FIG. 2 is a cross-sectional side view of a delivery system for high power Excimer laser energy utilizing a funnel-shaped energy coupler.

Referring now to FIG. 2, one embodiment of the delivery system for high energy Excimer laser light is illustrated in greater detail. The delivery system essentially comprises three basic elements. The first of these is the optical fiber 12. A fiber that has been found to be particularly suitable for use in the delivery of high energy Excimer laser light is a multi-mode fiber which has a relatively large core, or active area, relative to the area of its cladding, i.e., the outer skin of the fiber. The core is made of pure silica, e.g. quartz, which has been fused, and the cladding which surrounds this core comprises silica that has been doped with fluorine. In the context of the present invention, the fiber can be a single fiber or a bundle of fibers having a total diameter in the range of 100–2,000 microns. This entire structure can be surrounded by a protective flexible jacket 28 made, for example, of steel, nylon or a suitable polyurethane material.

A fiber of this construction can typically accommodate input energy up to a level around 30 mJ/mm$^2$. If the density of the energy is increased above this level, the input end of the fiber will be damaged or destroyed. Unfortunately, this density level is about the minimum that is required to produce ablation of calcified plaque, thus providing no margin of safety if the intended use of the delivery system is for angioplasty. Accordingly, in order to enable a higher level of energy to be conducted in the fiber, an energy coupler 30 can be provided at the input end of the fiber. In the embodiment illustrated in FIG. 2, this energy coupler comprises a section of fiber that has a larger cross-sectional area than the main portion of the fiber. This larger cross-sectional area gradually tapers to the nominal diameter of the fiber, so as to provide a funnel-shaped input section.

Production of such a shape on the end of the fiber can be accomplished through appropriate design of the die through which the silica is drawn to produce the fiber. By interrupting the drawing of the fiber, a bulbous mass remains at one end of the fiber. This mass can be cut and polished to produce the funnel-shaped input section.

In operation, the increased area of the funnel-shaped coupler decreases the input energy density for a given level of energy within the fiber. Accordingly, the area of the input end can be appropriately dimensioned to enable a sufficient amount of energy for ablation of tissue to be coupled into the fiber without damaging the input end. Once it has been coupled in, the density of the energy is increased by decreasing the cross-sectional area of the fiber within the tapered section, so that a greater amount of energy can be conducted within the fiber than would be possible without such a device.

Figure 3:
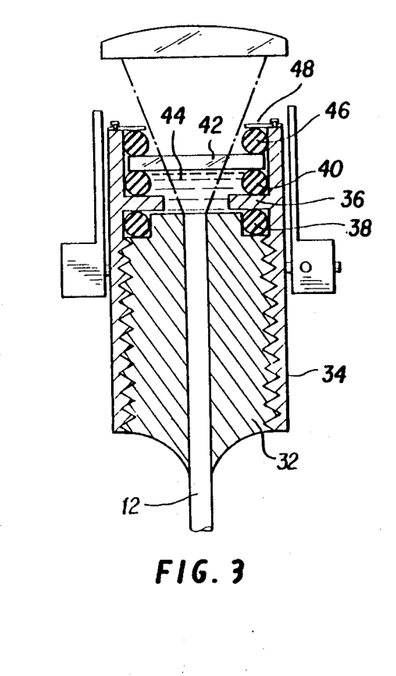
FIG. 3 is a cross-sectional side view of an alternate embodiment of an energy coupler.

An alternate embodiment of an energy coupler is illustrated in FIG. 3. In this embodiment, the optical fiber has a uniform diameter along its length and terminates at a flat polished end. The end section of the fiber is encased within a ferrule 32 made of a suitable material such as brass, for example. An aluminum casing 34 having an annular ring 36 projecting from the inner wall thereof is threaded onto the ferrule. A teflon O-ring 38 disposed between the end of the annular ring 36 and the ferrule provides a watertight seal between the casing and the ferrule. A second O-ring 40 is disposed on top of the annular ring and supports a glass plate 42 made of z-cut quartz, for example. This arrangement forms a fluid-tight cavity 44 between the ferrule 32, the casing 34 and the glass plate 42. The glass plate can be held in place by means of a third O-ring 46 and a clamping ring 48 disposed on the top of the casing. The fluid tight cavity is filled with liquid which acts as a buffer to the input end of the fiber, enabling laser energy having a relatively high density to be coupled into the fiber without damage thereto. The liquid within the cavity can be distilled and de-ionized water or it can be a transparent oil having an index of refraction that is matched to that of the fiber 12, for example.

The third feature of the delivery system is a lens 50 that can be provided at the distal end of the fiber. This lens operates to further increase the density of the energy once it emerges from the distal end of the fiber by reducing its cross-section to an area smaller than the fiber itself.

Figure 4A:
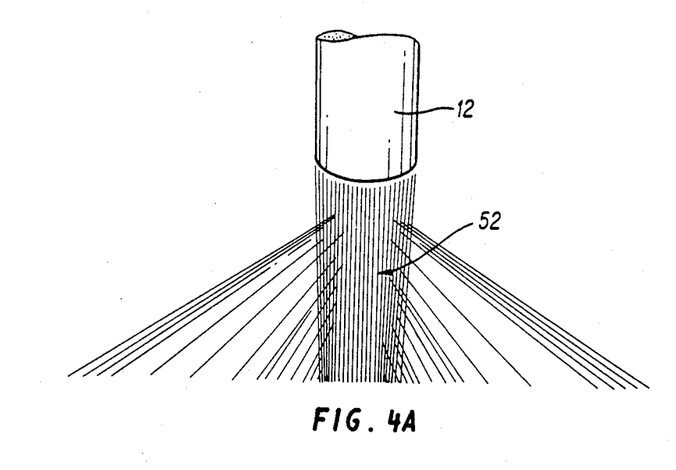
FIGS. 4A and 4B are illustrations of the light pattern which emerges from the distal end of the lensed fiber-optic waveguide.
Figure 4B:
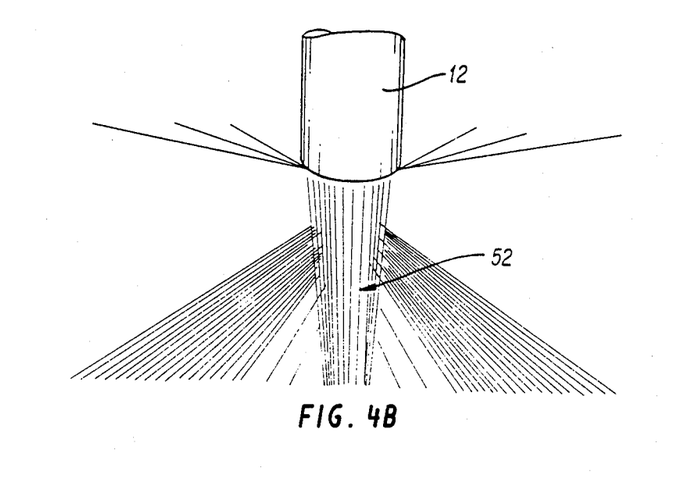

Referring to FIGS. 4A and 4B, two examples of the focused light pattern which emerges from the lens at the end of the optical fiber are shown. As can be seen, a majority of the light emerging from the optical fiber converges upon a focal point or plane 52. Basically, the distance of this focal point from the end of the fiber is determined by the radius of curvature of the lens. In addition, a small amount of the light diverges upon exiting from the optical fiber, so that the resulting light pattern at the focal point consists essentially of an extremely bright spot at the center of the focal point surrounded by a concentric area of lower illumination. As described in greater detail hereinafter, this outer area of lower illumination that is produced by the divergent light rays can be used with advantageous results in an angioplasty system.

Preferably, the lens 50 on the end of the optical fiber is integral with the fiber, i.e. formed from the material of the fiber itself. For example, a micro-torch can be used to melt the flat polished distal end of the tip to a predetermined spherical curvature under a microscope. Alternatively, the lens can be a discrete element separate from the fiber itself and adhered thereto by suitable means which minimizes light reflection at the fiber/lens interface.

Thus, with the combination of the pure silica fiber, the energy coupler 30 that enables a greater level of energy to be conducted through the fiber and the lens 50 at the distal end which converges the output energy onto a smaller area to thereby increase its density, an amount of high power laser energy that is sufficient to produce an incision can be safely transmitted through an optical fiber waveguide without the risk of damage to the fiber.

As noted above, one particular application for which the laser delivery system is particularly well suited is the field of angioplasty. In such an application, the optical fiber for the delivery of the laser energy can also be used to deliver the visible light that illuminates the interior of the vessel. While it is desirable to focus the laser energy so as to increase the density level, the opposite effect is normally preferred for the visible light. In other words, it is preferable to illuminate as wide an area as possible in order to give the physician a full view of the blood vessel in the vicinity of the end of the fiber. As shown in FIGS. 4A and 4B, although most of the energy is concentrated at the focal point 52, some of the light rays diverge upon emergence upon the fiber. It is possible to make use of this divergent light to perform the illumination function. It has been found that the amount of light which diverges away from the focal point is generally sufficient to provide enough illumination in the blood vessel to enable the physician to adequately observe the ambient area.

Figure 5:
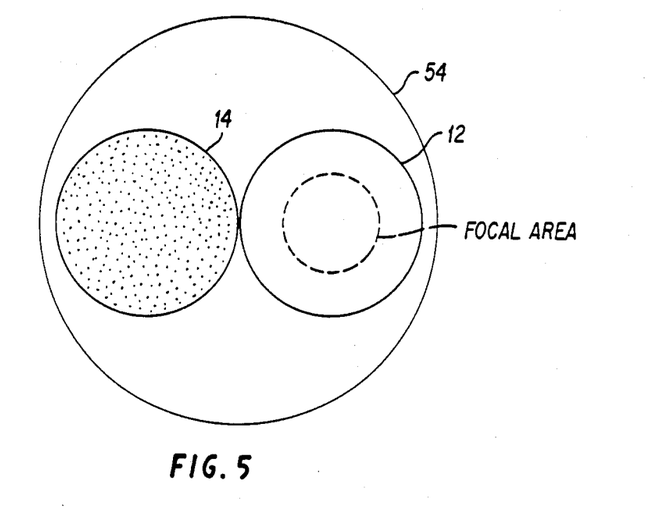
FIG. 5 is a cross-sectional end view of the two fibers that are employed in the laser and image delivery system of the present invention.

Thus, the angioplasty system need only utilize two optical fibers 12 and 14, one to deliver the laser and visible light energy and the other to return the image to a video camera for monitoring. These two fibers can be placed in a side-by-side arrangement, as illustrated in FIG. 5. Preferably, each fiber has a diameter of about 0.5 mm. They can be encased in a catheter 54 which has an outer diameter that is only slightly greater than 1 mm. The extra space present between the inner wall of the catheter and the optical fibers can be used as a flushing channel, thus making possible the use of the system within most coronary arteries.

Alternatively, separate light waveguides can be used for the laser energy and the visible light to provide a depth of field reference for the physician. More particularly, one of the more difficult tasks in the viewing of a body cavity or blood vessel through an endoscope or an angioscope is the determination of the size and location of a given object in the field of view. An inherent characteristic of the wide angled lens found in these devices is the fact that it distorts the scene and has no specific focal point. This problem is particularly noticeable when the viewing takes place through a single image guide that is located within a tunnel-like environment, such as a blood vessel that is obstructed by a non-uniform three-dimensional lesion.

Figure 6:
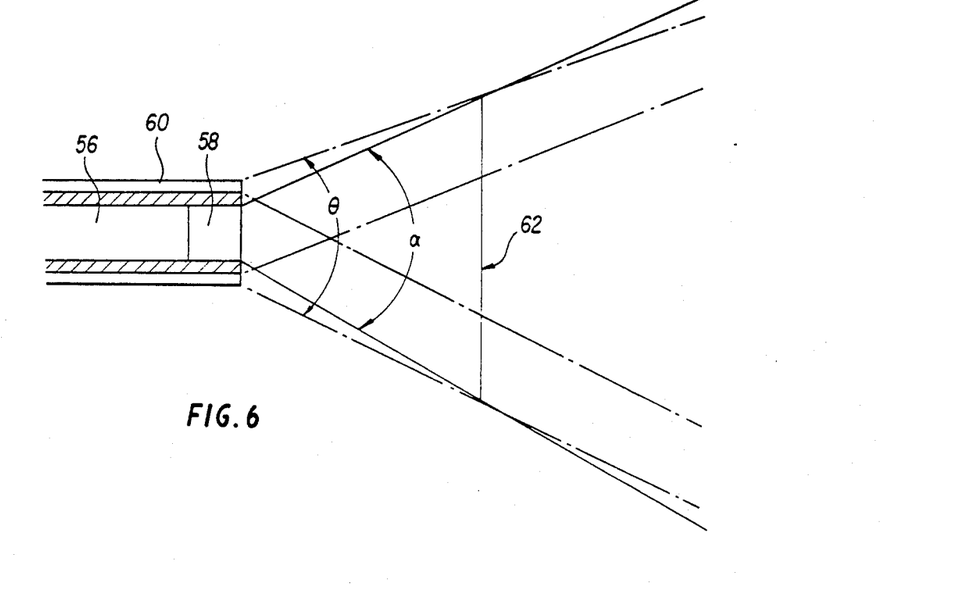
FIG. 6 is a side view of an alternate embodiment of a laser and image delivery system that provides a reference viewing plane within a narrow conduit.

In accordance with another feature of the present invention, however, this drawback can be eliminated by utilizing an illumination beam which has a smaller divergence angle than the field of view provided by the objective lens on the imaging waveguide. Referring to FIG. 6, the image waveguide 56, which can consist of a single optical fiber or a bundle of fibers, terminates in an objective lens 58 having a field of view which subtends the angle α. This image waveguide is surrounded by illuminating light waveguides 60 which project light that diverges over an angle β. In a conventional endoscope or angioscope, θ is greater than α so that the entire field of view is illuminated. However, in accordance with one aspect of the present invention, θ is less than α. These angles are determined by the numerical aperture (N.A.) of each of the waveguides 56 and 60, which is in turn related to the index of refraction of the material from which the core and cladding of the waveguide are made. Through appropriate adjustment of these two angles by proper selection of the materials for the waveguides, the illuminating field can be made to intersect the field of view of the lens 58 at a reference plane 62. For example, the N.A. of the image waveguide 56 could be 0.35 and that for the light waveguides 60 can be 0.20 to provide a reference plane that is about 2 mm from the end of the lens 58.

In practice, when an object is viewed through the image waveguide, the light reflected from that object will completely fill the field of view only when it is positioned at the reference plane 62. If the object is farther away from the lens than the reference plane, the illuminated portion of the object will be less than the total field of view, i.e., a dark circle will appear around the object. Alternatively, if the object is closer to the lens than the reference plane, it will appear blurred. Thus, the physician can determine the exact location of the distal end of the fiber relative to the viewed object, and hence the size of the object, by adjusting the position of the fiber until the illuminated image completely fills the field of view.

Figure 7:
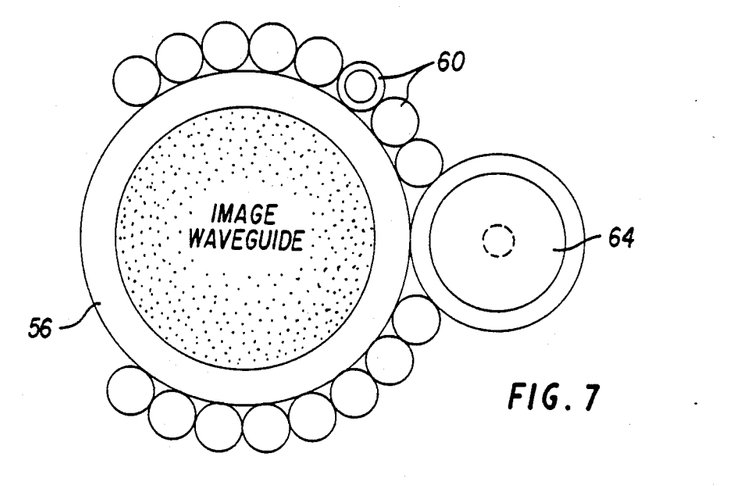
FIG. 7 is an end view of the system of FIG. 6 as incorporated in an angioplasty system.

The incorporation of this principle into an angioplasty system is illustrated in FIG. 7, which comprises the distal end view of the optical fibers. The image waveguide 56 and a lensed laser waveguide 64 are located in a side-by-side arrangement. A plurality of smaller light waveguides 60 are provided around most or all of the remaining circumference of the image waveguide, so that the beam of illuminating light will be concentric with the field of view of the image waveguide. By way of example, the image waveguide can have a diameter of about 1 mm., the laser waveguide can be about 0.5 mm. in diameter and the light waveguides can have a diameter between 0.10 and 0.15 mm.

It will be appreciated by those of ordinary skill in the art that the present invention can be embodied in other specific forms without departing from the spirit or essential characteristics thereof. The presently disclosed embodiments are therefore considered in all respects to b illustrative and not restrictive. The scope of the invention is indicated by the appended claims rather than the foregoing description, and all changes that come within the meaning and range of equivalents thereof are intended to be embraced therein.

What is claimed is:

1. A system for the delivery of pulsed laser light having high peak energy utilizing an optical waveguide, wherein said waveguide comprises an optical fiber having an energy conducting core of substantially pure silica and further including an energy coupler between one end of said fiber and a laser source for enabling energy pulses having a predetermined energy level to be coupled into said fiber and the energy level of said pulses to be maintained without damage to said fiber.

2. The delivery system of claim 1 further including a lens at the opposite end of said fiber for concentrating the energy emerging from said end into a convergent beam.

3. The delivery system of claim 2 wherein said lens is formed from the material of the fiber and integral therewith.

4. The delivery system of claim 2 wherein said optical fiber has a cladding which surrounds said substantially pure silica core, said core having a larger cross-sectional area than said cladding.

5. The delivery system of claim 1 wherein said energy coupler comprises a section of said fiber having a relatively large cross-sectional area at the end of said fiber and a tapered portion which reduces to a relatively small cross-sectional area to form a funnel-shaped input section.

6. A system for the delivery of high energy Excimer laser light utilizing an optical waveguide, wherein said waveguide comprises an optical fiber made of substantially pure silica and an energy coupler comprising a cavity that is filled with a liquid medium and that has a window transparent to laser energy on one side thereof and is in communication with one end of the fiber at the opposite side thereof to couple energy pulses having a predetermined energy level into said fiber without damage to said fiber.

7. The delivery system of claim 6 wherein said liquid medium is water.

8. The delivery system of claim 6 wherein said liquid medium is an oil having an index of refraction which is approximately the same as that of said optical fiber.

9. An angioplasty system, comprising:
  a source of visible light;
  a source of laser light energy;
  means for combining visible light and laser light from said sources to propagate them along a common path;
  a first fiber-optic waveguide which receives the visible light and laser light propagating along said path at one end thereof and conducts them to the distal end thereof;
  a lens on said distal end of said first waveguide for producing a pattern of light in which a majority of the light energy is focussed upon a focal point and a relatively small quantity of the light energy emitted from the distal end of said first waveguide is divergent;
  a second fiber-optic waveguide disposed alongside said first waveguide for receiving and conducting the image of an area illuminated by visible light emerging from said first waveguide; and
  means for viewing an image conducted by said second waveguide.

10. The angioplasty system of claim 9 wherein said viewing means includes a video coupler connected to said second waveguide, means for converting said image into a video signal, and a monitor for receiving said signal and displaying said image.

11. The angioplasty system of claim 9 wherein said source of laser light energy is an Excimer laser, and further including an energy coupler at said one end of said first waveguide for coupling laser pulses having a predetermined energy level into said first waveguide without damage thereto.

12. A system for viewing internal cavities that provides a plane of reference to assist in determining the relative location and size of a viewed object, comprising:
- a first fiber-optic waveguide having an objective lens at the distal end thereof, said lens having a predetermined numerical aperture defining a field of view;
- a plurality of second fiber-optic waveguides disposed around the periphery of said first waveguide, said second waveguides having a numerical aperture smaller than that of said first waveguide so that light emerging from the distal ends of said second waveguides is spread over an area of illumination which subtends an angle less than said field of view to thereby intersect the same;
- means for projecting visible light into the other ends of said second waveguides; and
- means for viewing an image conducted in said first waveguide.

13. The viewing system of claim 12 wherein said viewing means comprises a video coupler connected to the other end of said first waveguide, means connected to said video coupler for converting said image into a video signal, and a monitor for receiving said signal and displaying said image.

14. A system for the delivery of pulsed laser energy, comprising a fiber-optic waveguide made of substantially pure silica and an energy coupler including a cavity that is filled with a liquid medium and that has a window transparent to laser energy on one side thereof and is in communication with one end of the waveguide at the opposite side thereof for coupling energy pulses into said waveguide without damage to said waveguide, said energy pulses having a density that is sufficient to damage said waveguide in the absence of said coupler.

15. A system for the delivery of pulsed laser energy, comprising a source of pulsed laser energy, a fiber-optic waveguide having an energy conducting core of substantially pure silica and receiving the laser energy from said source at one end thereof, and a lens at the opposite end of said waveguide for focussing at least a majority of the energy emitted from said opposite end onto a focal point.

16. The delivery system of claim 15 further including an energy coupler at said one end of said waveguide for coupling energy pulses into said waveguide without damage to said waveguide said energy pulses having a density that is sufficient to damage said waveguide in the absence of said coupler.

* * * * *